United States Patent
Duncombe et al.

(10) Patent No.: US 12,196,748 B2
(45) Date of Patent: Jan. 14, 2025

(54) SELF-ASSEMBLED NANOPARTICLE FILM FOR NANOSTRUCTURE-INITIATOR MASS SPECTROMETRY (NIMS)

(71) Applicants: National Technology & Engineering Solutions of Sandia, LLC, Albuquerque, NM (US); The Regents of the University of California, Oakland, CA (US)

(72) Inventors: Todd A. Duncombe, Oakland, CA (US); Trent R. Northen, Walnut Creek, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

( * ) Notice: Subject to any disclaimer, the term of this patent is extended or adjusted under 35 U.S.C. 154(b) by 379 days.

(21) Appl. No.: 16/518,855

(22) Filed: Jul. 22, 2019

(65) Prior Publication Data
US 2019/0346436 A1    Nov. 14, 2019

Related U.S. Application Data

(63) Continuation of application No. PCT/US2017/068027, filed on Dec. 21, 2017.
(Continued)

(51) Int. Cl.
G01N 33/543 (2006.01)
G01N 33/68 (2006.01)
H01J 49/04 (2006.01)

(52) U.S. Cl.
CPC ... *G01N 33/54346* (2013.01); *G01N 33/6851* (2013.01); *H01J 49/0418* (2013.01)

(58) Field of Classification Search
None
See application file for complete search history.

(56) References Cited

U.S. PATENT DOCUMENTS 6,649,138 B2   11/2003   Adams et al.
7,951,572 B2   5/2011    Kim et al.
(Continued)

FOREIGN PATENT DOCUMENTS

WO   2009061313   5/2009
WO   2013036885   3/2013
(Continued)

OTHER PUBLICATIONS

International Preliminary Report on Patentability and International Search Report/Writen Opinion, PCT/US2017/068027. Jul. 23, 2019.
(Continued)

*Primary Examiner* — Xiaoyun R Xu
(74) *Attorney, Agent, or Firm* — Robin C. Chiang; LAWRENCE BERKELEY NATIONAL LABORATORY

(57) ABSTRACT

The present invention provides for a composition for ionizing a target comprising: a substrate comprising a plurality of nanoparticles bound to a surface of the substrate, which allows one to directly extract undesired contaminants during passive sample drying without require manual interventions, such as washing and vortexing.

18 Claims, 17 Drawing Sheets

Related U.S. Application Data

(60) Provisional application No. 62/448,947, filed on Jan. 20, 2017.

(56) References Cited

U.S. PATENT DOCUMENTS

| | | | |
|---|---|---|---|
| 9,125,596 | B2 | 9/2015 | Leclerc et al. |
| 10,240,180 | B2 | 3/2019 | Northen et al. |
| 10,386,371 | B2 | 8/2019 | Bowen et al. |
| 10,672,601 | B2 | 6/2020 | Northen et al. |
| 10,822,634 | B2 | 11/2020 | Northen et al. |
| 11,164,733 | B2 | 11/2021 | Gao et al. |
| 11,339,434 | B2 | 5/2022 | de Raad et al. |
| 11,353,467 | B2 | 6/2022 | Louie et al. |
| 11,366,122 | B2 | 6/2022 | Hia et al. |
| 2007/0110671 | A1* | 5/2007 | Chamberlin ........... B82Y 30/00 428/323 |
| 2015/0330992 | A1 | 11/2015 | Northen et al. |

FOREIGN PATENT DOCUMENTS

| | | |
|---|---|---|
| WO | 2014093552 | 6/2014 |
| WO | 2014116856 | 7/2014 |
| WO | 2017062481 | 4/2017 |
| WO | 2017214177 | 12/2017 |

OTHER PUBLICATIONS

International Search Report/Writen Opinion, PCT/US2017/068027. Feb. 20, 2018.

Kurczy et al., "Comprehensive Bio-Imaging with Fluorinated Nanoparticles Using Breathable Liquids." Nature Communications. 6:5998, (2015) 8 pages.

Gao et al., "Application of Black Silicon for Nanostructure-Initiator Mass Spectrometry," Anal. Chem. 88 (3), 1625-1630 (2016).

DeRond et al,, "High throughput screening of enzyme activity with mass spectrometry imaging." Curr Opin Biotechnol, 2015, 31, 1-9 (2015).

Blackledge et al., "Polyethylene membrane as a sample support for direct matrix-assisted laser desorption/ionization mass spectrometric analysis of high mass proteins" Anal Chem, 67 (5), 843-848 (1995).

Duncombe et. al., "Directed Drop Transport Rectified from Orthogonal Vibrations via a Flat Wetting Barrier Ratchet" Langmuir, 28(38), 13765-13770 (2012).

Oyola-Reynoso et al., "Recruiting physisorbed water in surface polymerization for bio-inspired materials of tunable hydrophobicity," Mater. Chem. A 2016, 4 (38), 14729-14738.

Law et al., "Recent advances in SALDI-MS techniques and their chemical and bioanalytical applications" Anal. Bioanal. Chem. 399 (8), 2597-2622. (2011).

Northen et al., "Clathrate nanostructures for mass spectrometry" Nature, 449 (7165), 1033-1036 (2007).

Kurczy, M.; Northen, T.; Trauger, S.; Siuzdak, G. In in Mass Spectrometry Imaging of Small Molecules; He, L., E., Ed.; Springer: New York; p. 141-149 (2015).

Dimitrakopoulos et al., "Organic Thin Film Transistors for Large Area Electronics" Adv. Mater. No. 2, 99-117 (2002).

Duncombe et al., "Insulator Nanostructure Desorption Ionization Mass Spectrometry" Anal. Chem, 90, 965-9661 (2018).

DeRond et al., "Versatile synthesis of probes for high-throughput enzyme activity screening", Anal Bioanal Chem 405:4969-4973 (2013).

* cited by examiner

SELF-ASSEMBLED NANOPARTICLE FILM FOR NANOSTRUCTURE-INITIATOR MASS SPECTROMETRY (NIMS)

CROSS-REFERENCE TO RELATED APPLICATIONS

This application claims priority as a continuation application of PCT International Patent Application No. PCT/US2017/068027, filed Dec. 21, 2017, which claims priority to U.S. Provisional Patent Application Ser. No. 62/448,947, filed on Jan. 20, 2017, both of which are hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the fields of analyte analysis and detection.

BACKGROUND OF THE INVENTION

There is a demand for extremely sensitive and non-destructive analytical techniques, for use in a wide variety of fields including biological and chemical assays. Mass spectrometry is one widely-used analytical method, which relies on ionization of a target molecule. Matrix-assisted laser desorption/ionization mass spectrometry (MALDI), which relies on a traditional preparation method, is limited by the necessity of co-crystallization of the analyte in a matrix. In addition, MALDI sensitivity, especially for low molecular weight analytes, is often limited by background noise due to ionization of matrix molecules. More recently-developed methods including DIOS have shown some success, but are limited in analyte scope.

NIMS is a matrix-free laser desorption ionization (LDI) substrate that traditionally leveraged laser-resonant etched-silicon nanostructures and initiator molecules for high sensitivity detection of adsorbed small molecules, lipids, and peptides in LDI-MS [1]. Kurczy et al. [2] demonstrated that spotted perfluorodecanethiol bound AuNPs could be used to directly analyze tissue sections. Previous salt fractionation protocols require manual interventions, such as washing [3] or vortexing [4].

SUMMARY OF THE INVENTION

The present invention provides for a composition for ionizing a target comprising: a substrate comprising a plurality of nanoparticles bound to a surface of the substrate, which allows one to directly extract undesired contaminants during passive sample drying without require manual interventions, such as washing and vortexing. The nanoparticle can be bound to the substrate in manner, such as the surface of the substrate is functionalized in a manner that allows nanoparticles to bind to the surface.

The present invention also provides for a method for ionizing a target, comprising: providing a semiconductor substrate; applying an nanoparticle to the substrate such that the nanoparticle is bound to the substrate; delivering a target to the substrate such that the target binds to the nanoparticle to form a target-loaded substrate; and irradiating the target-loaded substrate.

The present invention also provides for a device comprising a self-assembled, nanostructured fluorocarbon film as a nanostructure-initiator mass spectrometer (NIMS) substrate for the detection of small molecules, peptides, lipids, and nimzymes, wherein the device has a limit of detection down to at least 100, 200, 300, 400, 500, 600, 700, 800, or 900 femtomols to 10, 20, 30, 40, 50, 60, 70, 80, or 90 attomols, depending on the analyte, having a performance matching MS performance of previously published NIMS technologies cited herein. Previous NIMS technologies required expensive and time consuming wet or plasma etching procedures (T. R. Northen, O. Yanes, M. T. Northen, D. Marrinucci, W. Uritboonthai, J. Apon, S. L. Golledge, A. Nordström, and G. Siuzdak, "Clathrate nanostructures for mass spectrometry.," Nature, vol. 449, no. 7165, pp. 1033-6, Oct. 2007; T. De Rond, P. Peralta-Yahya, X. Cheng, T. R. Northen, and J. D. Keasling, "Versatile synthesis of probes for high-throughput enzyme activity screening," Anal. Bioanal. Chem., vol. 405, no. 14, pp. 4969-4973, 2013; J. Gao, M. de Raad, B. P. Bowen, R. N. Zuckermann, and T. R. Northen, "Application of Black Silicon for Nanostructure-Initiator Mass Spectrometry," Anal. Chem., vol. 88, no. 3, pp. 1625-1630, February 2016) (the preceding publications are hereby incorporated by reference). In contrast, the NIMS nanostructured fluorocarbon does not require a clean room or expensive it equipment. The polymer-based NIMS fabrication can be achieved by chemical vapor deposition (CVD) in 30 or fewer minutes and requiring only an oxygen plasma system, a vacuum, a desiccator, a hot plate, a silicon wafer, and perfluorooctyltrichlorosilane (FOTS).

The fabrication procedure of the device comprises:
1. A silicon wafer is treated with oxygen plasma for 2 to 5 minutes. A pressure of 650 mTorr is used.
2. The silicon wafer is then placed under vacuum in a desiccator with 200 μL solution of FOTS for 5 minutes at room temperature.
3. The desiccator is then sealed and placed on a 150° C. hot plate for 10 minutes. The surface temperature of the wafer reaches 90° C. during this time.
4. The desiccator is then removed from the hotplate and the vacuum is released. The fluorocarbon wafer is immediately ready for use.

FOTS molecule assembles directly atop the silicon surface to form a nanostructured fluorocarbon film. Due to the nature of its trichlorosilane binding moiety on FOTS, it binds both to the oxide groups on the surface as well as self-polymerizes to form a nanostructured surface (see attached SEM images). While it has been shown previously that FOTS CVD deposition form this type of structure (S. Oyola-Reynoso, I. D. Tevis, J. Chen, B. S. Chang, S. Çinar, J.-F. Bloch, and M. M. Thuo, "Recruiting physisorbed water in surface polymerization for bio-inspired materials of tunable hydrophobicity," J. Mater. Chem. A, vol. 4, no. 38, pp. 14729-14738, 2016; hereby incorporated by reference), the unique optoelectrical and MS properties of the polymer film has not been previously demonstrated.

The fabrication process of the device is exceedingly simple, cheap, and amenable for large surface area deposition and mass production. Further, as the coating is robust in a large range of solvents (e.g. acetone, isopropanol, water, etc.) it can be integrated into other microfabrication processes without a problem. It can be easily combined with photo-patterning to realize micropatterened fluorocarbon NIMS devices for additional functionality, such as salt-fractionation from samples.

The present invention also provides for the use of particles on a mass spectrometry surface to separate analytes and/or interferences, such as chromatographic separation of analytes and/or interferences.

In some embodiments, the composition, device or method does not comprise any gold, such as no nanoparticle or any composite nanoparticle comprises any gold.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
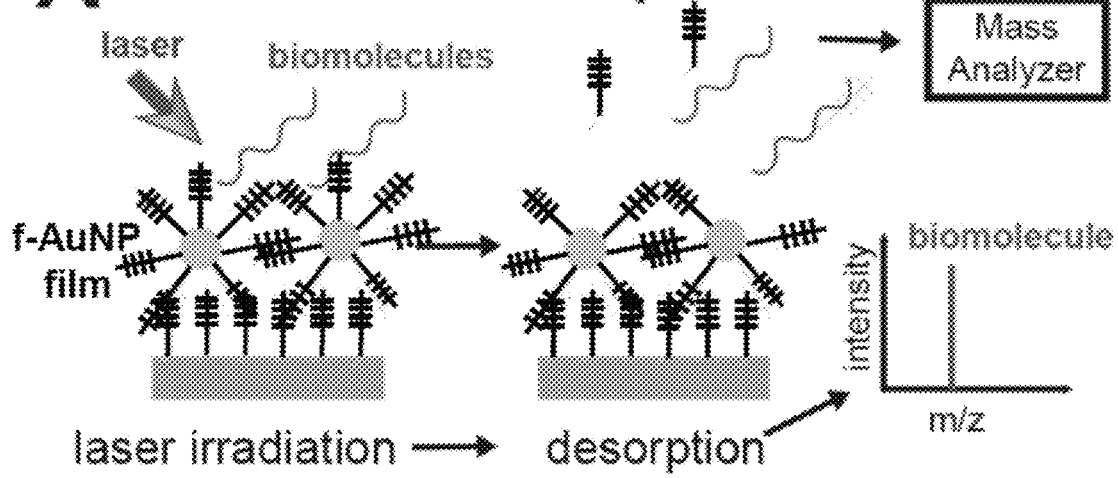
FIG. 1A shows fluorinated Au nanoparticle (f-AuNP) films are nanostructure-initiator mass spectrometry (NIMS) substrates for direct and high-sensitivity laser-based MS analysis of adsorbed molecules.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The present invention provides for a composition for ionizing a target comprising: a substrate comprising a plurality of nanoparticles bound to a surface of the substrate, which allows one to directly extract undesired contaminants during passive sample drying without require manual interventions, such as washing and vortexing. The nanoparticle can be bound to the substrate in manner, such as the surface of the substrate is functionalized in a manner that allows nanoparticles to bind to the surface.

In some embodiments, each nanoparticle of the plurality of nanoparticles comprises Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon.

In some embodiments, each nanoparticle is a composite nanoparticle comprising a coating comprising Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon.

In some embodiments, the composite nanoparticle comprises Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon coated by the coating.

In some embodiments, each nanoparticle is Gold.

In some embodiments, the nanoparticle is a halogenated nanoparticle.

In some embodiments, the nanoparticle is a fluorinated Gold nanoparticle (AuNP).

In some embodiments, the nanoparticle is sphere, rod, wire, or tube.

The nanoparticle can be any nanoparticle that is capable of binding the substrate. In some embodiments, the nanoparticle and the substrate independently comprise a carbon chain bound to the nanoparticle. The carbon chain can be straight or branched. In some embodiments, the carbon chain comprises a longest chain that is at least two, three, four, five, six, seven, eight, nine or ten carbon atoms long. In some embodiments, the carbon chain comprises a longest chain that is at most ten, twenty, thirty, forty, fifty, or 100 carbon atoms long. In some embodiments, the carbon chain comprises a longest chain that is from two, three, four, five, six, seven, eight, nine or ten to ten, twenty, thirty, forty, fifty, or 100 carbon atoms long. In some embodiments, the carbon chain comprises a longest chain that is from two to 100 carbon atoms long. In some embodiments, the longest chain is from eight to ten carbon atoms long. In some embodiments, the carbon chain is halogenated. In some embodiments, the carbon chain is fluorinated, chlorinated, or brominated.

In some embodiments, the nanoparticle and the substrate comprise carbon chains that are identical. In some embodiments, the nanoparticle and the substrate comprise carbon chains that are different wherein the nanoparticle is capable of binding to the substrate via the carbon chains of the nanoparticle and the substrate. In some embodiments, the carbon chain of the nanoparticle and carbon chain of the substrate differ by having longest carbon chains that differ in length by one, two, three, four, or five carbon atoms.

Methods of synthesizing the nanoparticle are disclosed by Kurczy et al. [2].

In some embodiments, the substrate comprises a semiconductor selected from the group consisting of Group IV semiconductors (e.g., diamond), Group I-VII semiconductors (e.g., CuF, CuCl, CuBr, CuI, AgBr, and AgI), Group II-VI semiconductors (e.g., BeO, BeS, BeSe, BeTe, BePo, MgTe, ZnO, ZnS, ZnSe, ZnTe, ZnPo, CdS, CdSe, CdTe, CdPo, HgS, HgSe, and HgTe), Group III-V semiconductors (e.g., BN, BP, BAs, AlN, AlP, AlAs, AlSb, GaN, GaP, GaSb, InN, InAs, InSb), sphaelerite structure semiconductors (e.g., MnS, MnSe, (3-SiC, Ga2Te3, In2Te3, MgGeP2, ZnSnP2, and ZnSnAs2), Wurtzite Structure Compounds (e.g., NaS, MnSe, SiC, MnTe, Al2S3, and Al2Se3), I-II-VI2 semiconductors (e.g., CuAlS2, CuAlSe2, CuAlTe2, CuGaS2, CuGaSe2, CuGaTe2, CuInS2, CuInSe2, CuInTe2, CuTlS2, CuTlSe2, CuFeS2, CuFeSe2, CuLaS2, AgAS2, AgAlSe2, AgAlTe2, AgGaS2, AgGaSe2, AgGaTe2, AgInS2, AgInSe2, AgInTe2, AgFeS2), and silicon.

In some embodiments, the semiconductor is a p-type semiconductor.

In some embodiments, the semiconductor is crystalline silicon.

In some embodiments, the semiconductor has a <100> orientation.

In some embodiments, the substrate is a black silicon substrate.

In some embodiments, the composition further comprises a target in contact with the nanoparticle.

In some embodiments, the target is a constituent of a sample selected from a biological sample, an environmental sample, a clinical sample, a forensic sample, or a combination thereof.

The present invention also provides for a method for ionizing a target, comprising: providing a semiconductor substrate; applying an nanoparticle to the substrate such that the nanoparticle is bound to the substrate; delivering a target to the substrate such that the target binds to the nanoparticle to form a target-loaded substrate; and irradiating the target-loaded substrate.

In some embodiments, irradiating the target-loaded substrate comprises irradiating the target-loaded substrate with a laser, an ion beam, or any combination thereof.

In some embodiments, delivering a target to the substrate comprises contacting a sample comprising the target to the substrate.

In some embodiments, the sample is a biological sample, an environmental sample, a clinical sample, a forensic sample, or a combination thereof.

In some embodiments, the target is selected from the group consisting of lipids, amino acids, small molecules, peptides, drugs, proteins, and any combination thereof. The method of claim 19, wherein the sample comprises a tissue, a cell, a biofluid, or a combination thereof.

In some embodiments, the invention utilizes self-assembly of the nanoparticles of the present invention to create micropatterned NIMS films. In some embodiments, the nanoparticle and substrate both comprise halogenated carbon chains (such as fluorinated carbin chain) and the invention utilizes halogen-mediated (such as fluorine-mediated) self-assembly of the nanoparticles of the present invention to create micropatterned NIMS films. The enables wafer-level batch-fabrication and enhances reproducibility of traditional NIMS substrates. The traditional NIMS substrates require HF etching [1] and are plagued with inconsistency from the initiator application step. In some embodiments, the invention comprises the use of micropatterned nanoparticle film which allows one to directly extract undesired contaminants during passive sample drying, which is unlike previous salt fractionation protocols that require manual interventions (e.g. washing [3] or vortexing [4]).

REFERENCES CITED

[1] J. Gao, et. al., *Anal Chem,* 2016, 88 (3), 1625.
[2] M. E. Kurczy, et. al., *Nat Comm,* 2015, 5998.
[3] T. Rond, et. al., *Curr Opin Biotechnol,* 2015, 31, 1.
[4] J. A. Blackledge and A. J. Alexander, *Anal Chem,* 1995, 67 (5), 843.
[5] T. A. Duncombe, et. al., *Langmuir,* 2012, 28(38), 13765.

The preceding publications are hereby incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Self-Assembled Gold Nanoparticle Film for Nanostructure-Initiator Mass Spectrometry with Passive On-Line Salt Fractionation Self-assembly of fluorinated-Au Nanoparticle (f-AuNP) films are a mass-producible fabrication methodology for generating nanostructure-initiator mass spectrometry (NIMS) substrates capable of high sensitivity detection of peptides (20 fmol). Further, through micropatterning of the f-AuNP film to create discrete wettability, we passively fractionate the hydrophobic molecules of interest from high-salt background environments for robust and predictable MS.

Figure 1B:
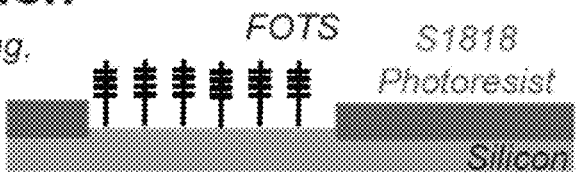
FIG. 1B shows fabrication of the f-AuNP film is mediated by a photo-patterned, covalently bound perfluorooctyl-trichlorosilane (FOTS) monolayer attached to a silicon wafer [5]. The FOTS-coated substrate is dipped into a 2 g/L solution of f-AuNP (2-4 nm diameter) in HFE 7500 for 10 min then dried. The S1818 photoresist is stripped with acetone, then washed in IPA, DI water and dried. The f-AuNPs are immiscible in any non-fluorinated oils. Therefore, the films are stable in stripping and washing.
Figure 1B:
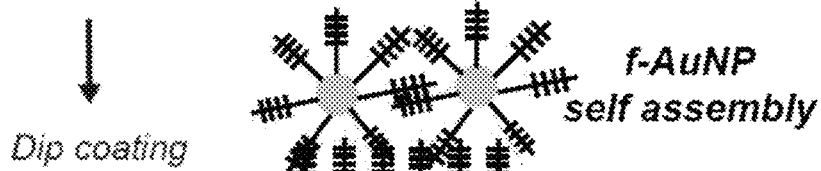
Figure 1C:
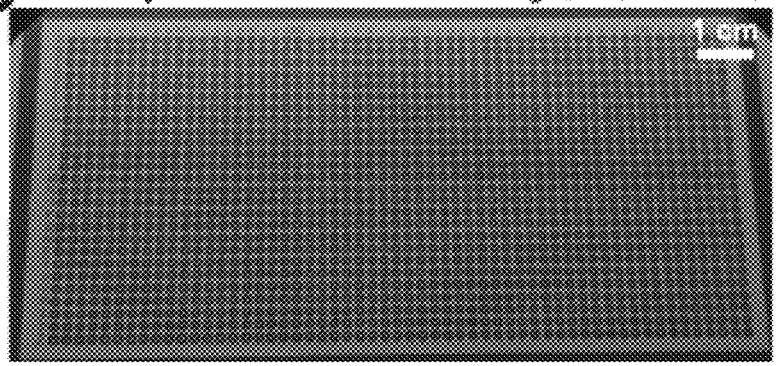
FIG. 1C shows the simplicity of fabrication enables scale up to batch wafer processing. The aluminum traces serve as a visual cue-f-AuNP patterns are not visible by eye.
Figure 1D:
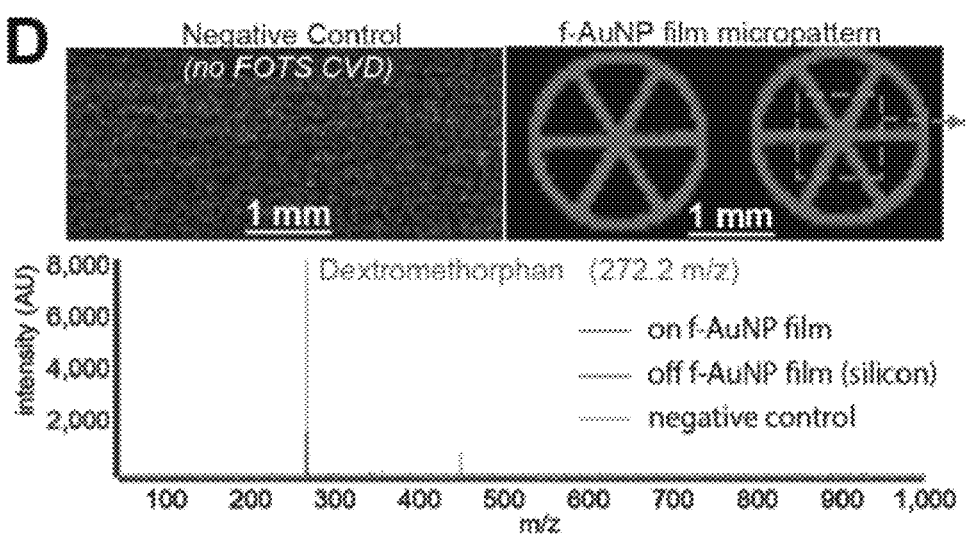
FIG. 1D shows substrates fabricated with FOTS and without were soaked in DI water containing 250 nM dextromethorphan for 1 hour and then imaged using mass spectrometry. The micro-patterned wheel shaped f-AuNP film is apparent in the mass spectra while no ionization occurred off-pattern or in the negative control.
Figure 1E:
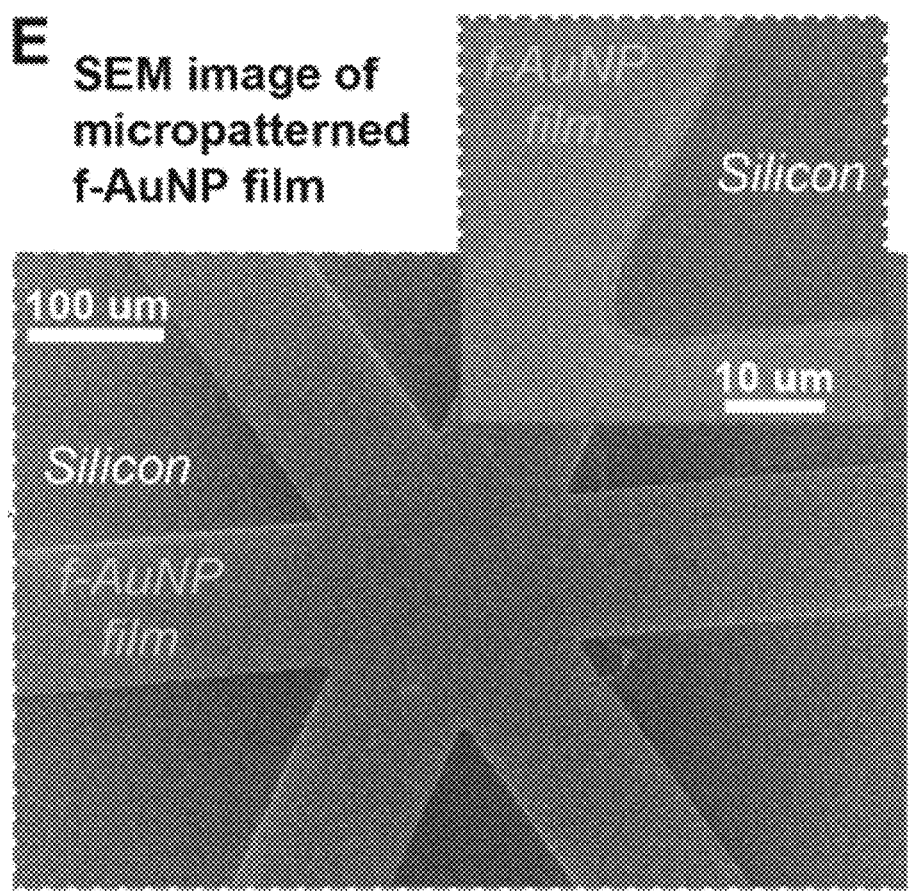
FIG. 1E shows Scanning Electron Microscopy (SEM) corroborated MS results—revealing the micro-patterned f-AuNP film.

The f-AuNP NIMS film is interfaced with by simply pipetting a sample of interest and letting it dry atop the surface. Positive mode LDI with a standard MALDI-MS, we used an AB Sciex 4800, enables direct interrogation of adsorbed lipids, small molecules, and peptides atop the surface (FIG. 1A). As displayed in FIG. 1B, the NIMS NP films are quickly fabricated utilizing fluorine-mediated nanoparticle self-assembly. First, the fluorine 'adhesion-molecule' perfluorooctyltrichlorosilane (FOTS) is covalently-patterned by chemical vapor deposition (CVD) on a S1818 resist photo-patterned silicon wafer which has been freshly O2 plasma treated. Then, we immersed the wafer for 10 min in a 2 g/L f-AnNP solution (2-4 nm diameter, perfluorodecanethiol functionalized [2]) in HFE 7500. After incubation, the substrate is dried and photoresist is stripped with acetone. We have scaled this approach to fabricate 1456 spot NIMS arrays (FIG. 1C). Mass spectrometry imaging and scanning electron microscopy confirm the fluorine-mediated self-assembly of the f-AuNP films capable matrix-free of direct LDI-MS analysis (FIG. 1D, FIG. 1E).

The structure of FOTS is:

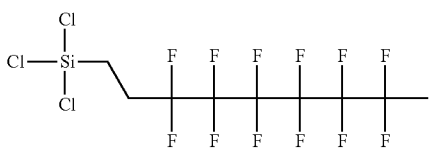

Figure 2A:
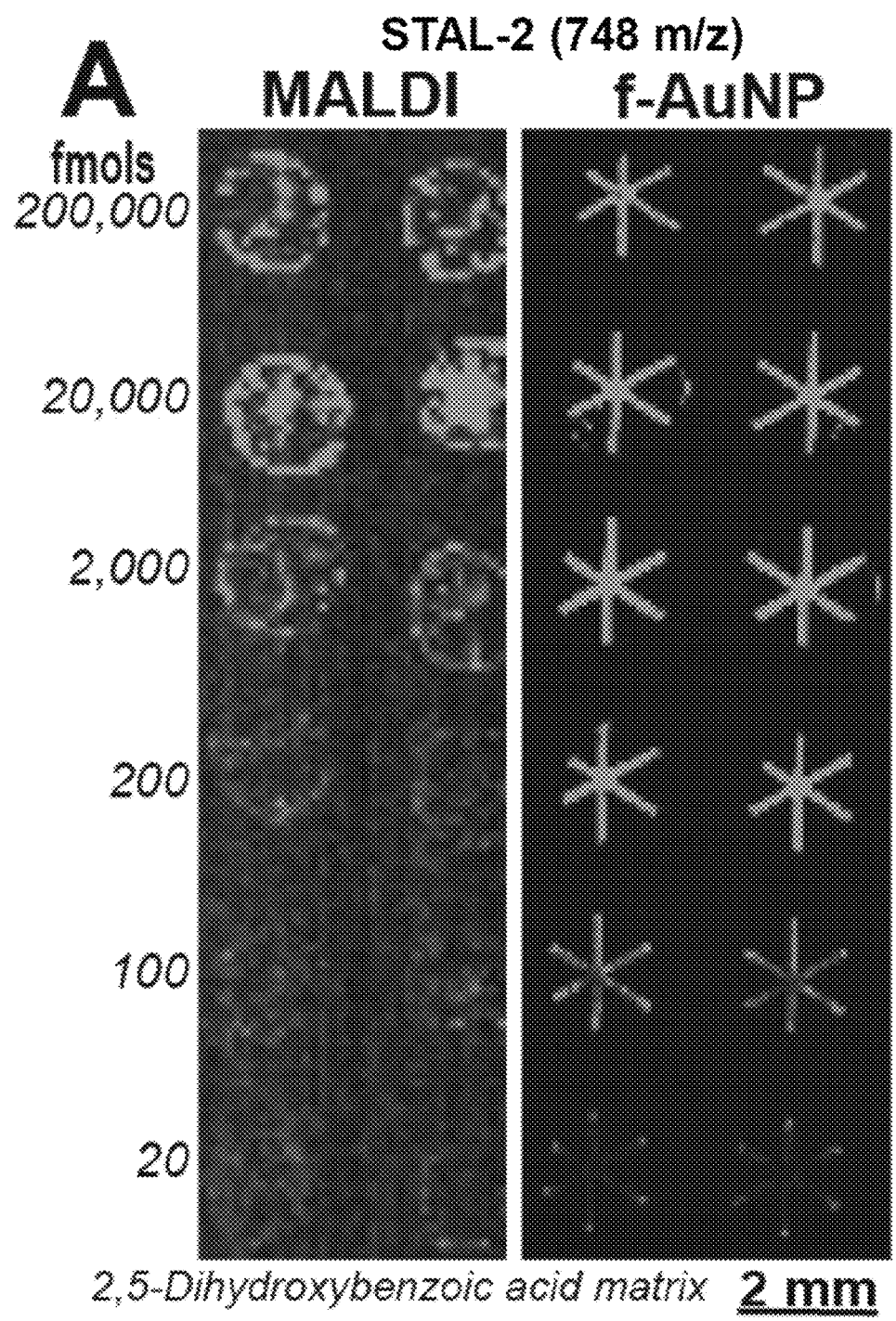
FIG. 2A shows f-AuNP films showing enhanced MS signal and limit of detection (LOD) over MALDI. The common MALDI matrix 2,5-dihydroxybenzoic acid (20 g/L, 50% EtOH) was compared to f-AuNP films for the detection of the peptide STAL-2 from 200,000 to 20 fmols.
Figure 2B:
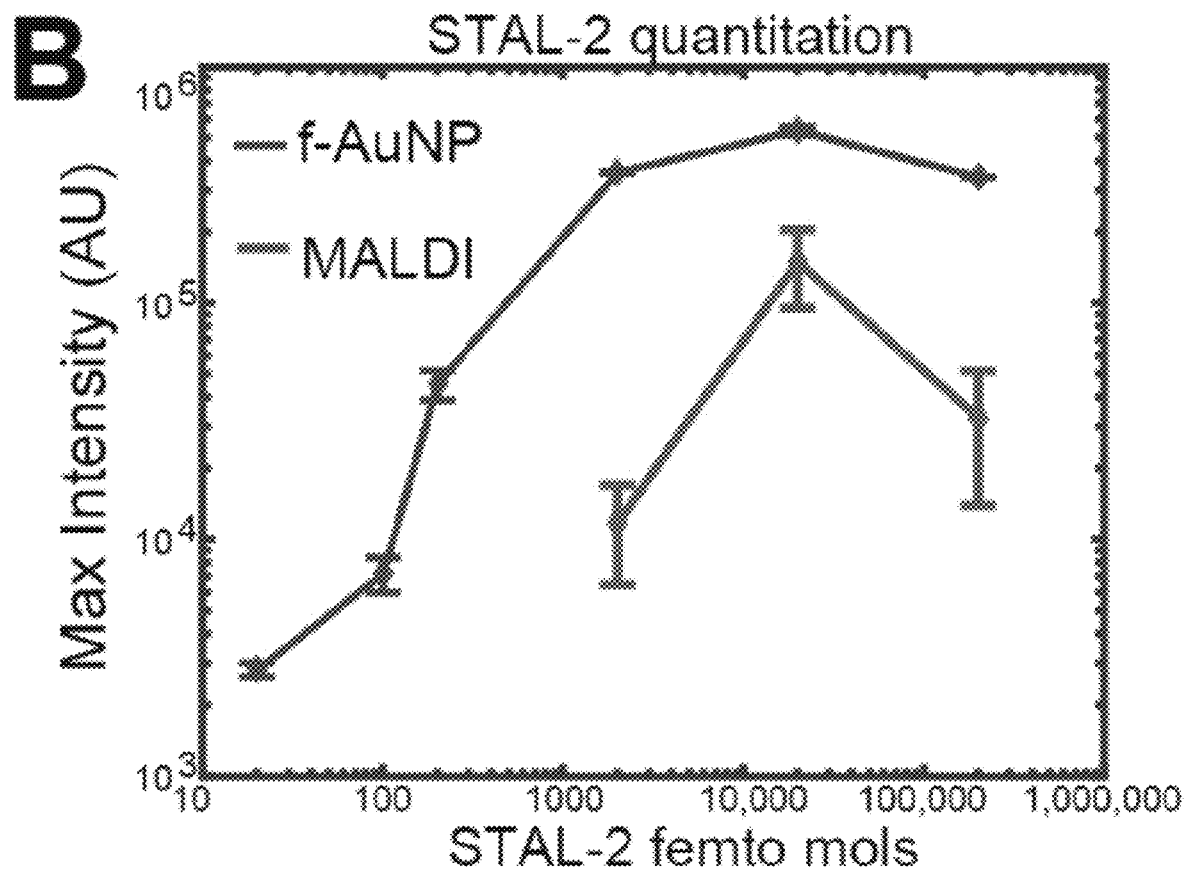
FIG. 2B shows a log-log plot of mols and max intensity with error bars (n=3) highlights a robust quantitative region between 20 and 2000 fmols. As expected for NIMS [1] the f-AuNP film had a STAL-2 LOD of ~20 fmols—while MALDI required 200 fmols.
Figure 2C:
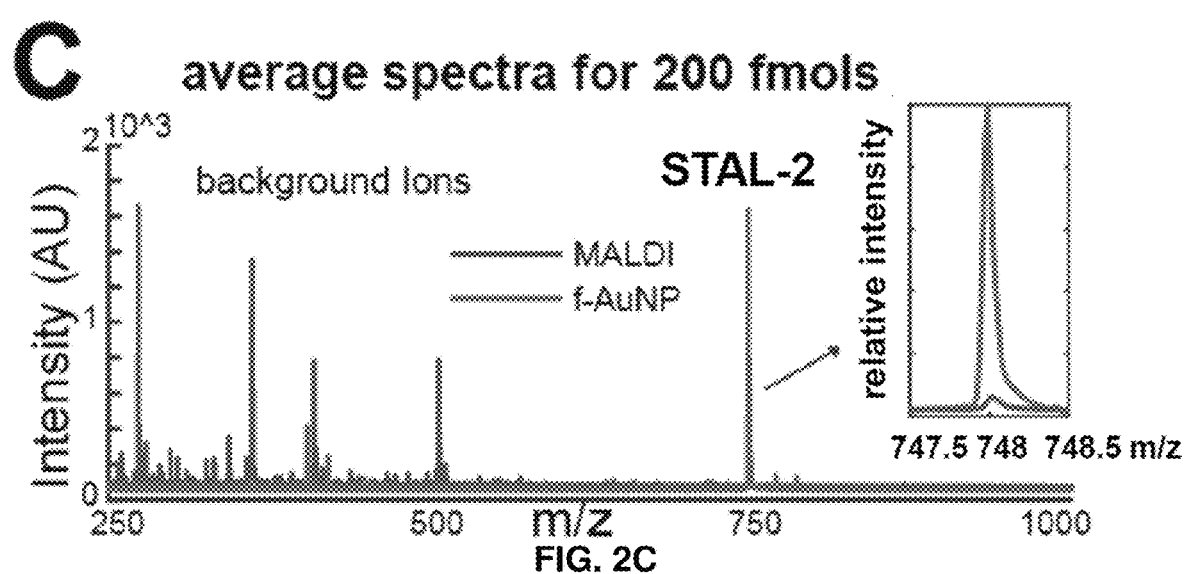
FIG. 2C shows average spot spectra are displayed for the 200 fmol samples for both conditions. In addition to the 15-times higher STAL-2 greater signal, the f-AuNP had a clean spectra devoid of dominant matrix ions.

We evaluated the sensitivity of our f-AuNP films against a common matrix-assisted laser desorption ionization. (MALDI) matrix in FIG. 2A, FIG. 2B, and FIG. 2C (2,5-dihydroxybenzoic acid, 20 g/L, 50% EtOH). FIG.2A displays the MS image of a MALDI plate and a micro-patterned f-AuNP film spotted with samples containing between 200, 000 to 20 fmols of the peptide STAL-2. As expected for NIMS, we observed enhanced peptide sensitivity with a limit of detection of less than 20 fmols (FIG. 2B). Further, as shown in FIG. 2C, the f-AuNP had considerably lower background ions than the MALDI matrix.

Figure 3A:
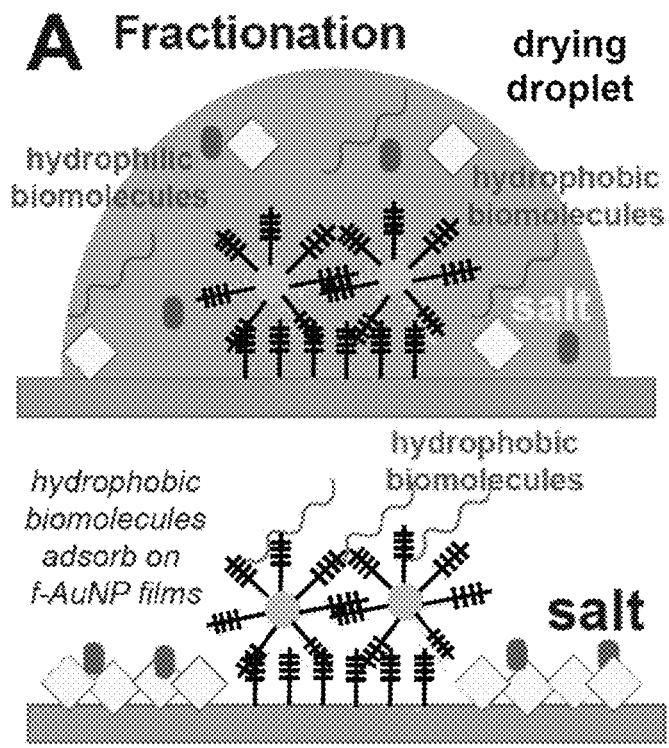
FIG. 3A shows micro-patterned f-AuNP films enable passive and on-line fractionation of salt from complex samples. A sample is spotted directly atop the f-AuNP film and allowed to dry During this process, hydrophobic molecules adhere to the f-AuNPs while salts and hydrophilic components dry atop the bare silicon region.
Figure 3B:
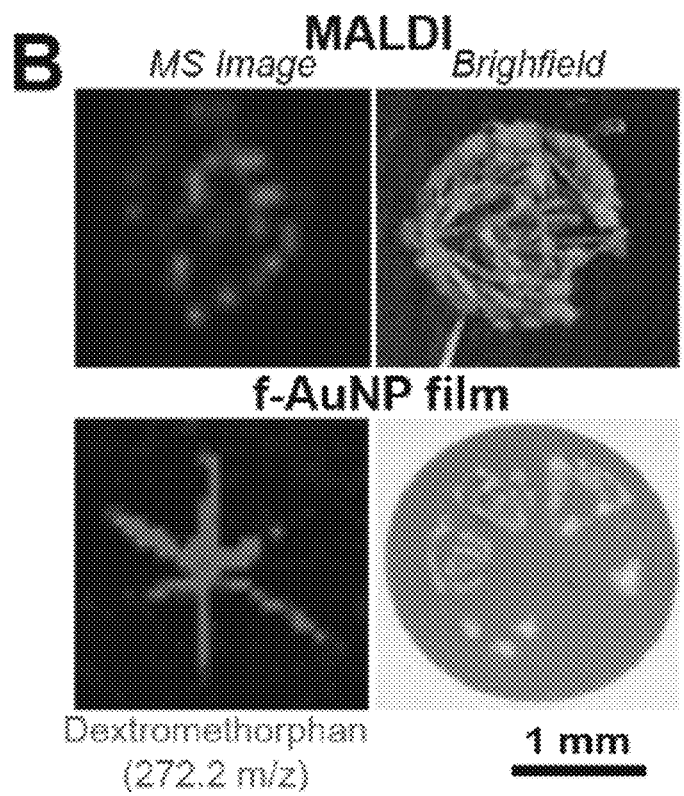
FIG. 3B shows droplets containing 500 fmols of dextromethorphan and 1 M NaCl were analyzed with MALDI (same conditions as FIG. 2) f-AuNP. For MALDI, a web of salt and matrix conceals ions of interest (top panels). For the micro-patterned f-AuNP film, dextromethorphan adhered to the f-AuNP film whereas salts were preferentially excluded from those regions (bottom panels). This predictable fractionation enables high-throughput analysis of complex samples.

In FIG. 3A and FIG. 3B we dried samples of 1 M NaCl and 500 fmol dextromethorphan on a MALDI plate and a micro-patterned f-AuNP film. The f-AuNP film fractionates passively. Salt dries atop the bare-silicon regions while dextromethorphan is adsorbed onto the f-AuNP regions. Predictable on-line fractionation could be applied for the analysis of complex samples such as cell lysate or solutions that contain MS-suppressing surfactants.

Example 2

Insulator Nanostructure Desorption Ionization Mass Spectrometry (INDI-MS)

Laser desorption ionization is widely used in mass spectrometry (LDI-MS) to analysis a broad range of compounds, ranging from metabolites to biopolymers. Surface Assisted Laser Desorption Ionization (SALDI) is an approach of gas phase ion generation that uses laser excitation of mass spectrometry surfaces, typically using nanostructured surfaces for mass spectrometry (MS) based analyses. These approaches are distinct from the widely used Matrix Assisted Laser Desorption Ionization (MALDI) in that SALDI surfaces do not require the addition of matrix, photochemical compounds used in MALDI that facilitate analyte desorption and ionization. Since matrix compounds ionize and are typically added in large excess versus analyte, a major focus of SALDI technologies is to facilitate analysis of small molecules that may be obscured by matrix ions. SALDI surfaces have been prepared from a wide range of conductive and semiconductive materials for example nanostructured silicon, carbon nanotubes (which can be highly conductive), metal nanoparticles, among others[3]. In addition to lack of matrix, many SALDI techniques have high sensitivity, for example nanostructure-initiator mass spectrometry (NIMS), which uses a perfluorous liquid 'initiator' to facilitate desorption coating initiator molecules4, is suitable for analyses of many small molecules, lipids, and peptides[5] with limits of detection at the yoctomole level[6].

Despite performance advantages, the challenges and complexities associated with fabrication of SALDI surfaces likely is a major factor that limits their use to labs specialized in nanofabrication. For example, NIMS surfaces are typically generated by anodic hydrofluoric acid (HF) etching of silicon, which requires extensive training, special equipment, and clean room access. Recently, a method of generating black silicon NIMS using plasma etching was developed.[2] While the technique eliminated the wet hydrofluoric acid step it unfortunately still requires highly specialized equipment typically only found in clean-rooms.

One promising alternative to solid-state fabricated nanostructures is organic polymers. In recent years organic electronics have been widely adopted in various optoelectronic applications, from light emitting diodes, to photodetectors, and organic solar cells. This is in large part due to their relative low cost, ease of fabrication, and their mechanical and chemical stability. Here a range of high-throughput fabrication procedures are used including chemical vapor deposition (CVD), sputtering, and spin coating.[8] It is known that non-conductive polymer arrays can alter the bandgap of semiconductor surfaces and corresponding plasmonics, and this is especially true for polymers containing electron withdrawing fluorines.

Herein is described the fabrication of nanostructures from perfluoroalkyl siloxanes for LDI-MS, as shown in FIG. 4. The resulting non-conductive organic "insulator" nanostructures combines the low-cost and simplicity of organic electronics fabrication with the efficient desorption of diverse metabolites of NIMS. This approach, insulator nanostructure desorption ionization (INDI) enables facile integration with photolithographic patterning, in this case for constructing passive desalting features. The resulting devices can be used to construct and test passive desalting/chromatography devices for analysis of bacterial extracts.

Experimental Section

The list of chemicals used is: FOTS, OTS, FOMECS, Acetone, IPA, Formic Acid, DI water, MALDI matrix, silver epoxy, aluminum coated wafers, silicon wafers, diamond cutter, photoresist, etc. The list of compounds used is: dextromethorphan, verapamil, pdc, stal-2, mastoparan, arginine. The list of equipment used is: 4800, 5800, SEM, UV-Vis equip, photo-induced exp (laser, oscilloscope, etc.), desiccator chamber, vacuum line, hot plate, oxygen plasma, etc.

INDI is fabricated as follows: Perfluorooctyltrichlorosilane (FOTS) is utilized to form INDI-MS substrates with the following simple and straightforward protocol. New silicon wafers (for example, n-type) are treated in an oxygen plasma for 5 minutes at 600 mTorr. They are then immediately placed in dessicator with a vial of 200 µL FOTS, followed by application of house vaccum (100 Torr) for 5 minutes. Then, the dessicators chamber is sealed to maintain the vacuum and transferred onto a 150° C. hot plate. The wafer temperature then decreases until it reaches 75° C. in 10 minutes. Once the wafer has cooled, the INDI-MS surfaces are ready to use immediately.

µINDI is fabricated as follows: Micropatterned INDI substrates incorporate several basic microfabrication approaches for generating chemical patterns and aluminum traces. 30 nm aluminum coated silicon wafers are treated with oxygen plasma, spun coat with S1818 photoresist, UV exposed, and developed to produce the desired physical mask prior to aluminum etching. The wafer is then placed into a glass container of Trace Aluminum Etchant heated at 60° C. until for approximately 5 minutes or until the desired aluminum has fully been removed. After a 5 minute soak in DI water and nitrogen drying, the wafer is placed in acetone to remove the remaining photoresist. After an IPA rinse, DI water rinses, and nitrogen drying, the wafer is again oxygen plasma treated and patterned with photoresist to produce the desired physical mask for the deposition of the INDI coating. The protocol described in the previous section for INDI deposition is then followed. Afterwards, to ensure the covalent attachment the wafer is hard baked for 30 minutes at 100° C. Finally, the remaining photoresist is removed in acetone, and then wafer is rinsed in IPA, DI water and blown dry with nitrogen.

Acoustic printing is performed using an EDC ATS-100 printer and a 10 nL deposition volume. Mass Spectrometry (MS) is performed with an AB Sciex TOF/TOF 5800 MALDI. MS imaging data is analyzed using OpenMSI.

Results and Discussions

Figure 4A:
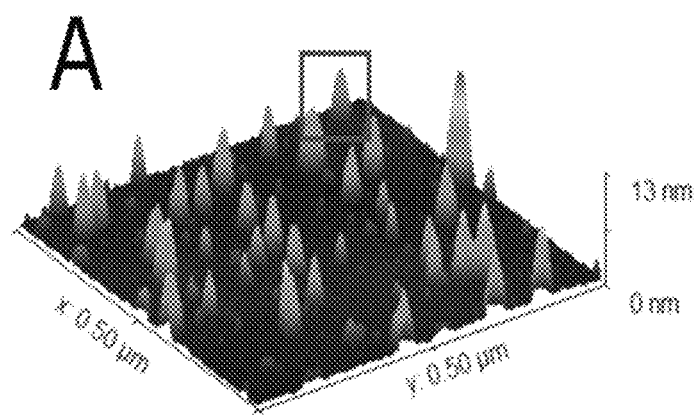
FIG. 4A shows an Insulator Nanostructure Desorption Ionization Mass Spectrometry (INDI-MS) utilizing a self-assembled perfluoroalkyl nanostructure to facilitate laser desorption ionization-MS (LDI-MS). Atomic force microscopy demonstrates the 10 nm to 50 nm diameter semielliptical nanostructures spaced by ~100 nm on INDI surfaces. INDI substrates are generated simply in 20 minutes using chemical vapor deposition (CVD) of perfluorooctyltrichlorosilane (FOTS).
Figure 4B:
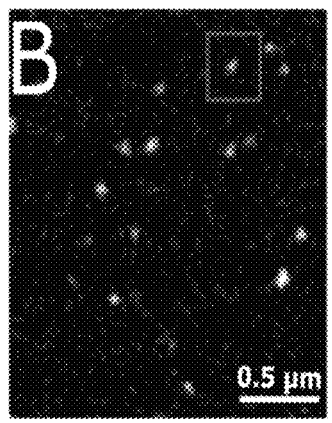
FIG. 4B shows an Insulator Nanostructure Desorption Ionization Mass Spectrometry (INDI-MS) utilizing a self-assembled perfluoroalkyl nanostructure to facilitate laser desorption ionization-MS (LDI-MS). Scanning electron microscopy demonstrate the 10 nm to 50 nm diameter semielliptical nanostructures spaced by ~100 nm on INDI surfaces. INDI substrates are generated simply in 20 minutes using chemical vapor deposition (CVD) of perfluorooctyl-trichlorosilane (FOTS).
Figure 4C:
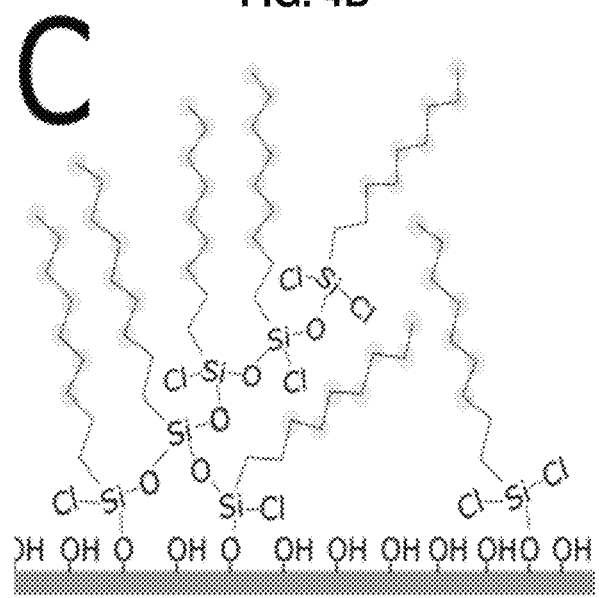
FIG. 4C shows an Insulator Nanostructure Desorption Ionization Mass Spectrometry (INDI-MS) utilizing a self-assembled perfluoroalkyl nanostructure to facilitate laser desorption ionization-MS (LDI-MS). FOTS binds atop a silicon oxide surface and to itself to form siloxane nanostructures decorated with perfluoroalkyls (yellow).
Figure 4D:
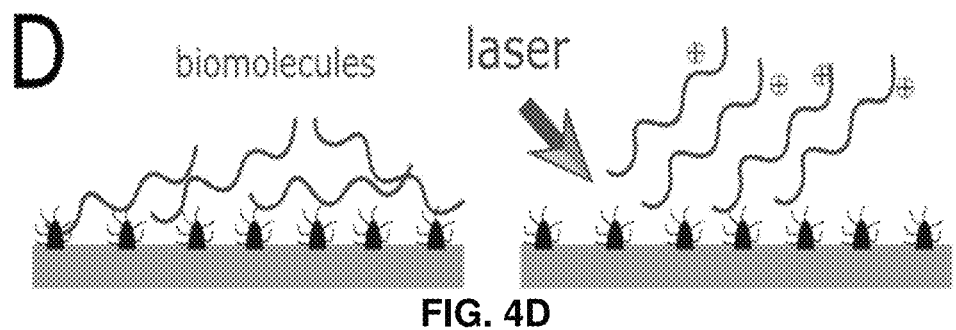
FIG. 4D shows an Insulator Nanostructure Desorption Ionization Mass Spectrometry (INDI-MS) utilizing a self-assembled perfluoroalkyl nanostructure to facilitate laser desorption ionization-MS (LDI-MS). LDI-MS is performed directly on the INDI surface to analyze adsorbed molecules.
Figure 4E:
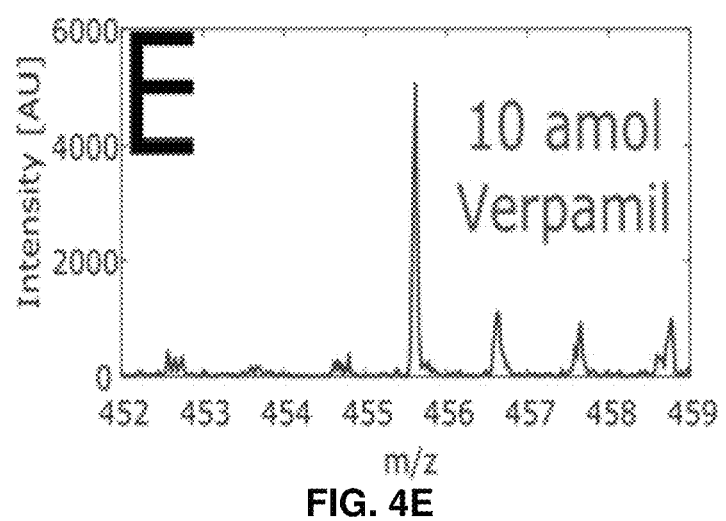
FIG. 4E shows an Insulator Nanostructure Desorption Ionization Mass Spectrometry (INDI-MS) utilizing a self-assembled perfluoroalkyl nanostructure to facilitate laser desorption ionization-MS (LDI-MS). LDI-MS is performed directly on the INDI surface to analyze adsorbed molecules, and is shown to have a limit of detection of down to 10 attomols for small molecule verapamil.
Figure 5A:
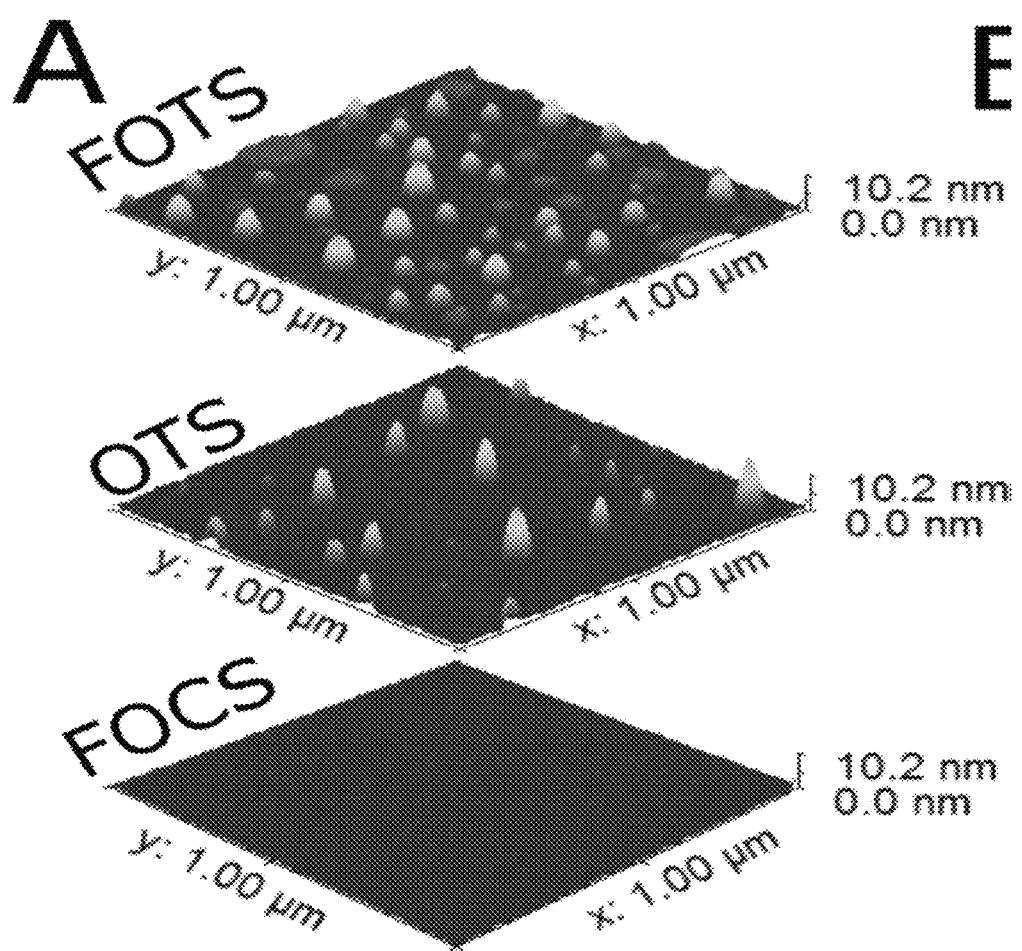
FIG. 5A shows a comparison with alternative insulator surface coatings indicates that INDI-MS surfaces require nanostructures and perfluorination. Control insulator silane surface coatings of octyltrichlorosilane (OTS, no fluorine) or perfluorooctydimethylchlorosilane (FOCS, single reactive site per molecule) are fabricated to generate surfaces lacking perfluorination or nanostructures, respectively. AFM characterization confirmed that the trivalent molecules, FOTS and OTS, form similar nanostructures, while the monovalent FOCS formed a monolayer with ~1 nm features.
Figure 5B:
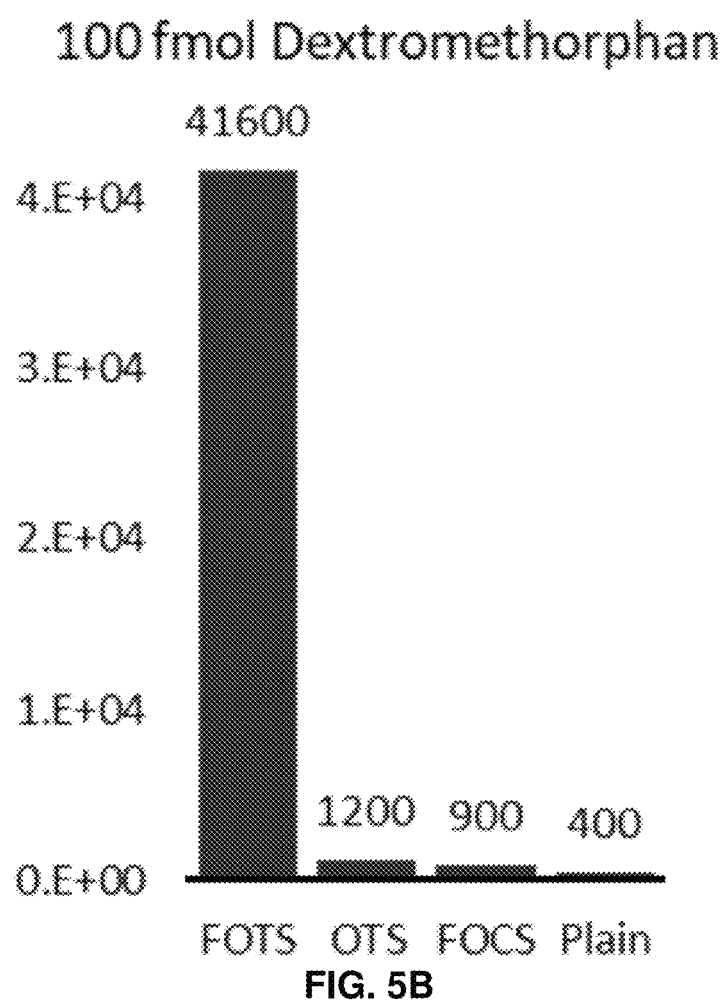
FIG. 5B shows a comparison with alternative insulator surface coatings indicates that INDI-MS surfaces require nanostructures and perfluorination. Control insulator silane surface coatings of octyltrichlorosilane (OTS, no fluorine) or perfluorooctydimethylchlorosilane (FOCS, single reactive site per molecule) are fabricated to generate surfaces lacking perfluorination or nanostructures, respectively. MS performance varied dramatically between FOTS, OTS, FOCS and plain silicon for the detection of 100 femtomols of dextromethorphan.

To fabricate INDI surfaces, an already ubiquitous fabrication technique is used: the chemical vapor deposition (CVD) of alkyltrichlorosilanes. Previously, it had been demonstrated that nanostructures can be directly generated via the self-assembly alkyltrichlorosilane during chemical vapor deposition[9]. The trichlorosilane chemical moiety is commonly used to attach a desired alkyl group to oxide surface. In the presence of water vapor and a silicon wafer, the three active reaction sites on the trichlorosilane rapidly form siloxane bonds with a silicon oxide surface, generating a silicone base polymer. Previously, it had been shown that the combined self- and surface-reaction of alkyl-trichlorosilanes surface during CVD results in the step-growth of bead-like nanostructures atop a surface[1], a process roughly depicted in FIG. 4A. To verify the formation of nanostructures, the substrates are accessed with scanning electron microscopy and atomic force microscopy (FIGS. 4B and 4C, respectively). Both measurements confirm the generation semielliptical nanostructures during the self-assembly process. The approximate nanostructures dimensions had a circular cross section of 50 nm, a height of 10 nm, and a nanostructure to nanostructure spacing ranging between 75 nm and 200.

FIGS. 5A to 5E show a comparison with alternative insulator surface coatings indicates that INDI-MS surfaces require nanostructures and perfluorination. Control insulator silane surface coatings of octyltrichlorosilane (OTS, no fluorine) or perfluorooctydimethylchlorosilane (FOCS, single reactive site per molecule) are fabricated to generate surfaces lacking perfluorination or nanostructures, respectively. Alternative coatings (FIG. 5A), MS performance of different monolayers (FIG. 5B), are light adsorption (FIGS. 5C and 5D) are shown. While the surfaces demonstrated a significant shifted response in photo-induced charge transfer, the fact that FOTS, OTS, and FOCS all shifted similarly indicates that this alone cannot explain the enhanced MS performance. Controls: OTS forms a similar nanostructured film during CVD deposition, but lacks fluorocarbon properties. In contrast, perfluorooctydimethylchlorosilane (FOMeCS) has an identical perfluorinated eight carbon alkyl as FOTS, but does not form the nanostructure because it cannot self polymerize. Both OTS and FOMeCS lack the enhanced MS properties seen for FOTS NIMS films. Demonstrating that both the nanostructure and the fluorocarbon features are necessary for the observed MS performance.

Figure 6:
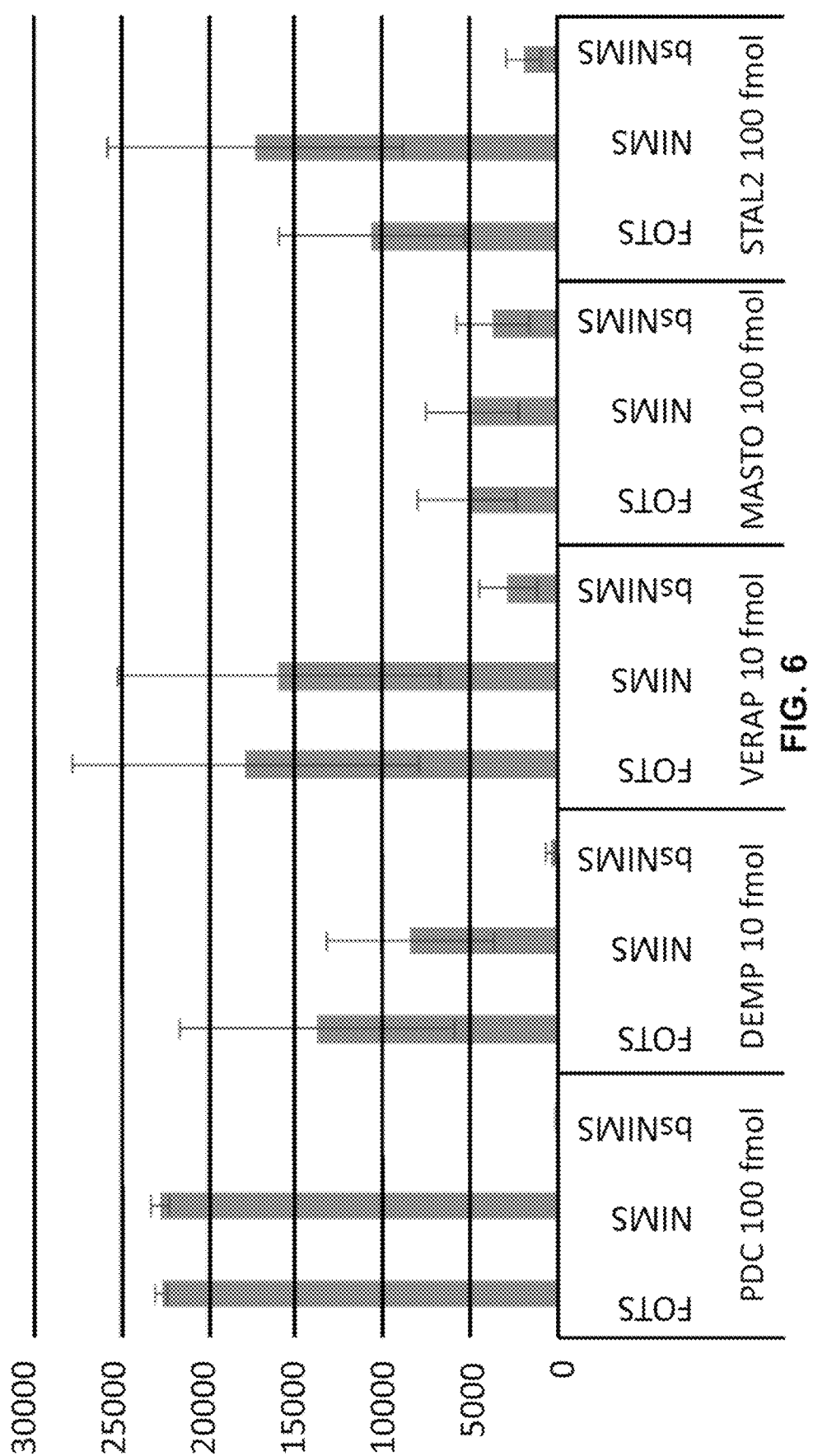
FIG. 6 shows an INDI-MS performs comparably to wet etched NIMS and better than black silicon NIMS (bsNIMS) for LDI-MS of peptides and small molecules between 10 and 100 fmols in abundance.

FIG. 6 shows an INDI-MS performs comparably to wet etched NIMS and better than black silicon NIMS (bsNIMS) for LDI-MS of peptides and small molecules between 10 and 100 fmols in abundance.

Figure 7:
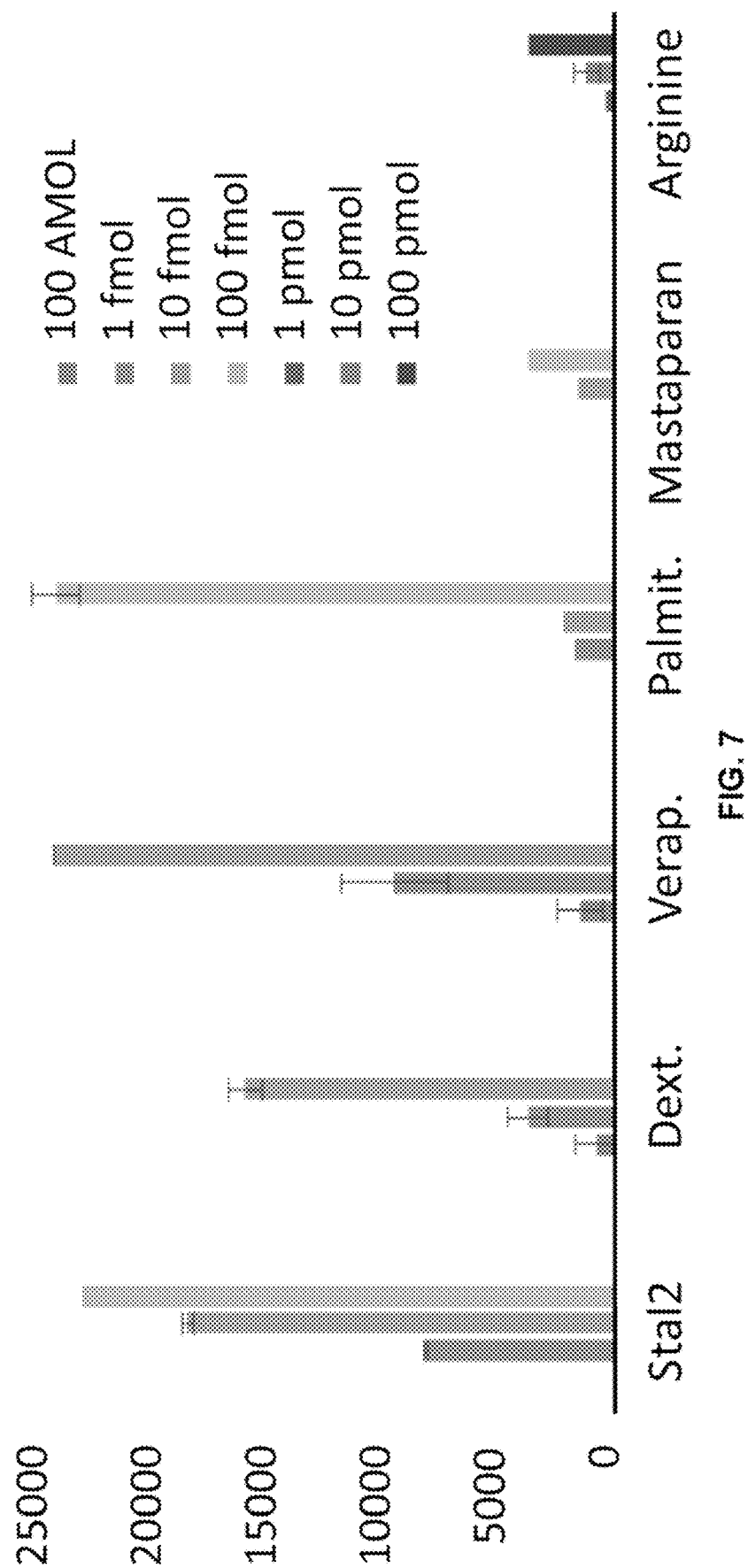
FIG. 7 shows the assessment for INDI-MS sensitivity for diverse small molecules. Acoustically printed 10 nL aqueous droplets with 0.2% formic acid containing a range of small molecules, peptides, amino acids, and fatty acids were analyzed with INDI-MS imaging.
Figure 8A:
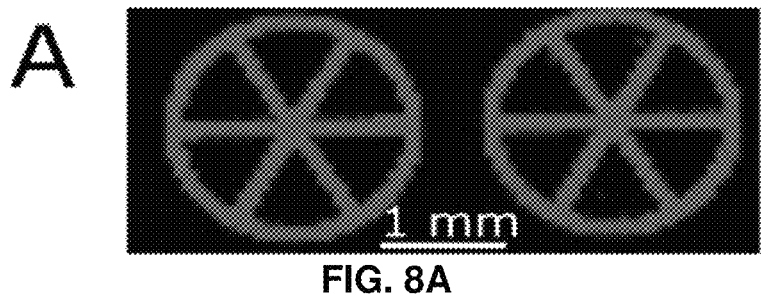
FIG. 8A shows micro-patterned INDI substrates facilitate passive desalting and fractionation of hydrophobic molecules from complex samples. MS image of micropatterned INDI substrate that had been soaked in 1 µM dextromethorphan. Photolithographically defined INDI patterns enable the direct fabrication of heterogenous surfaces consisting of hydrophobic/LDI-MS active regions (red) and hydrophilic/LDI-MS inactive regions (black).
Figure 8B:
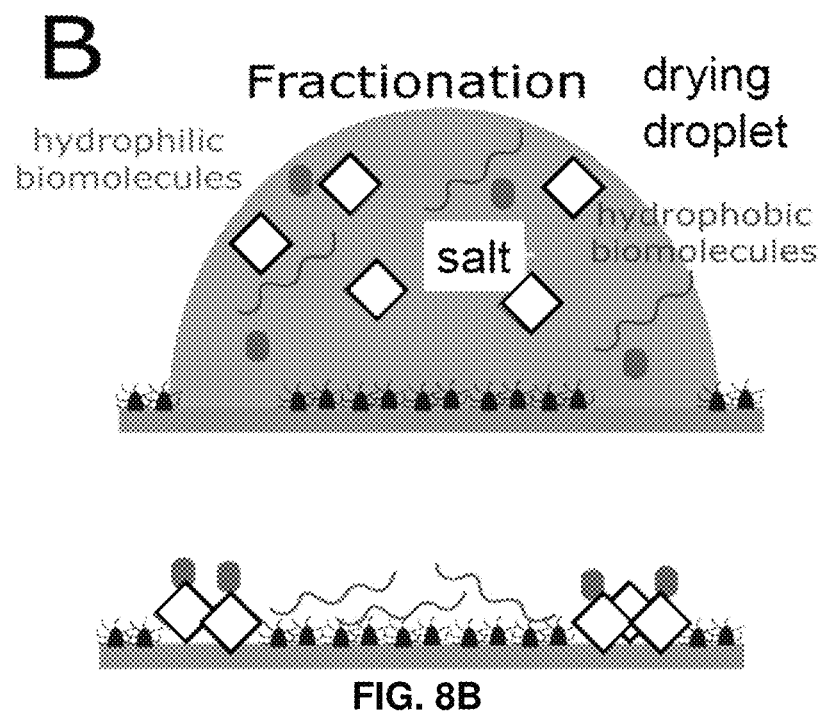
FIG. 8B shows micro-patterned INDI substrates facilitate passive desalting and fractionation of hydrophobic molecules from complex samples. As a droplet evaporates atop a microINDI substrate, hydrophobic molecules rapidly adsorb to the hydrophobic INDI region, while salts and hydrophilic molecules stay in solution until the evaporation is complete, and thus are deposited onto the bare silicon regions.
Figure 8C:
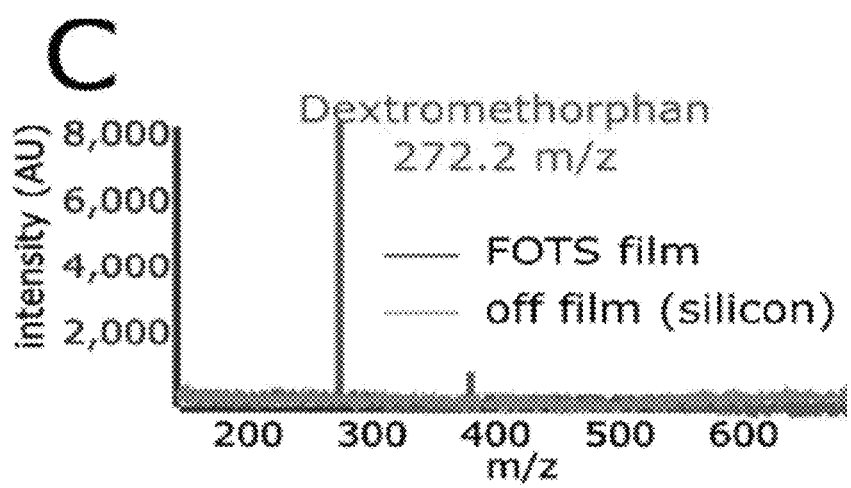
FIG. 8C shows micro-patterned INDI substrates facilitate passive desalting and fractionation of hydrophobic molecules from complex samples. The adsorbed hydrophobic molecules can be directly analyzed with LDI-MS.
Figure 8D:
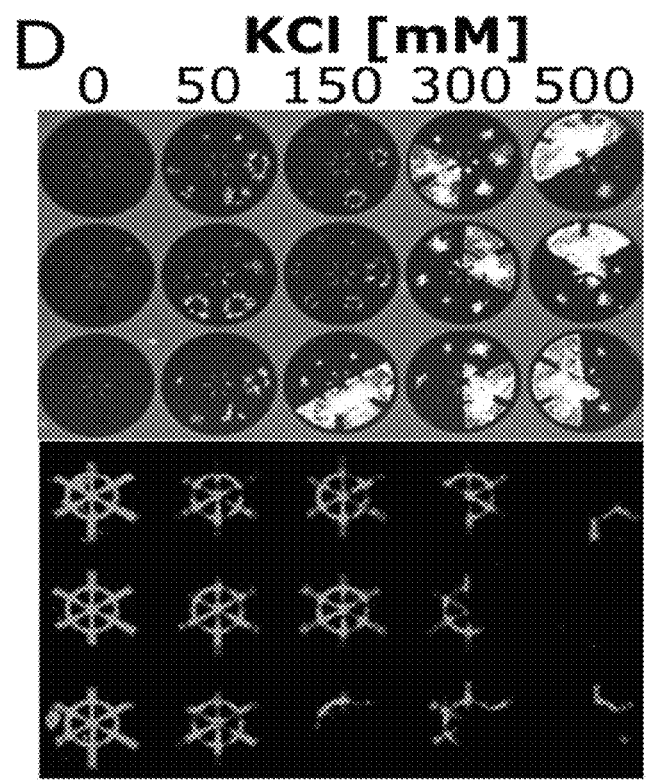
FIG. 8D shows micro-patterned INDI substrates facilitate passive desalting and fractionation of hydrophobic molecules from complex samples. Brightfield images show fractionation of salts into the designated silicon dioxide locations, while microINDI-MS imaging displays Stal-2 associated with the designated pattern.
Figure 8E:
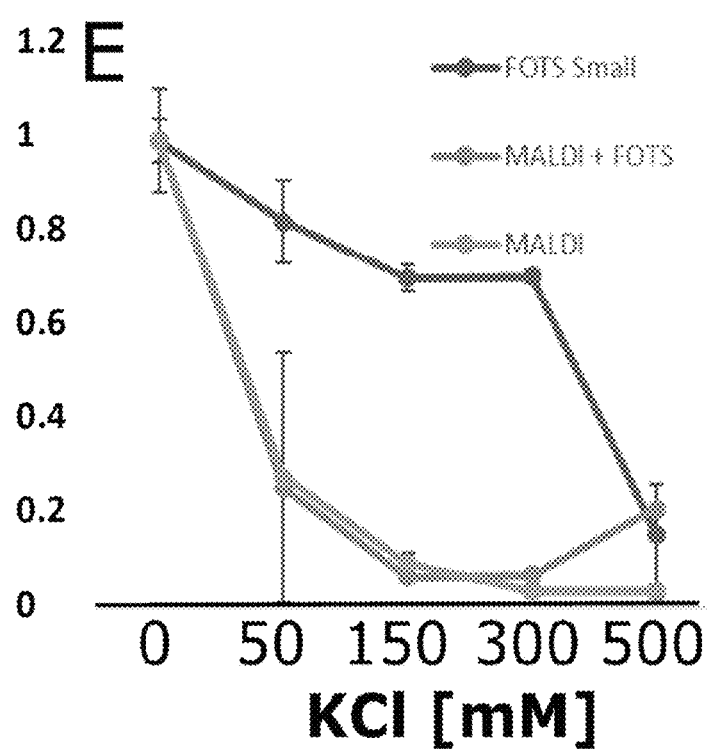
FIG. 8E shows micro-patterned INDI substrates facilitate passive desalting and fractionation of hydrophobic molecules from complex samples. Stal-2 quantitation shows demonstrates that microINDI fractionation enables comparable quantitation of Stal-2 from 0 to 300 mM KCl, while MALDI observed a sharp reduction of signal at only 50 mM KCl.

FIG. 7 shows the assessment for INDI-MS sensitivity for diverse small molecules. Acoustically printed 10 nL aqueous droplets with 0.2% formic acid containing a range of small molecules, peptides, amino acids, and fatty acids were analyzed with INDI-MS imaging. The limit of detection ranged down to $10^{-16}$ moles for dextromethorphan and verapamil, to $10^{-15}$ moles for STAL-2 and palmitoylcarnitine, and to $10^{-12}$ moles for arginine. Manual INDI-MS operation could be used to further improve the limit of detection by approximately 10-fold.[2]

FIGS. 8A to 8E show micro-patterened INDI substrates facilitate passive desalting and fractionation of hydrophobic molecules from complex samples. To demonstrate the utility of passive salt fractionation we created a dilution series of 1 picomol Stal-2 in 500 mM, 300 mM, 150 mM, 50 mM, and 0 M concentrations of KCl.

Figure 9:
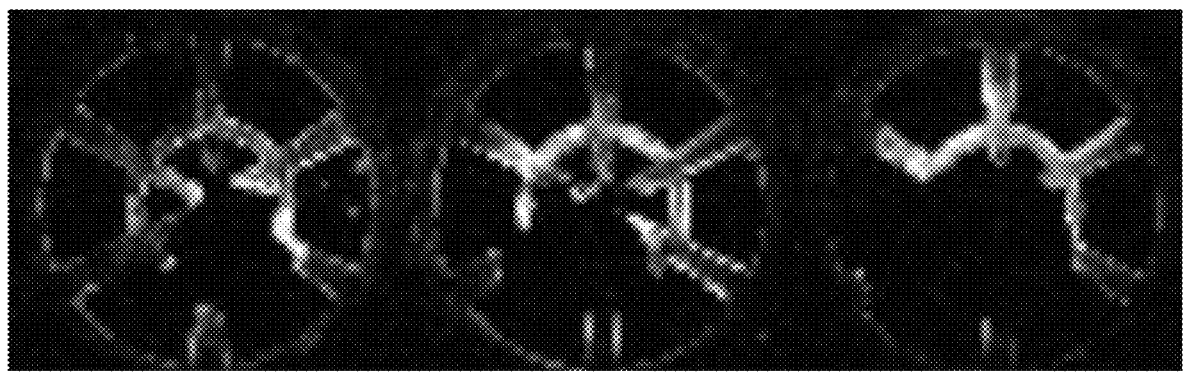
FIG. 9 shows a spent media demonstration. Example image. SepMut $1/30^{th}$ dilution. Red: 1641, Green: 1754.25, and Blue: 1219.25.

FIG. 9 shows a spent media demonstration. Example image. SepMut $\frac{1}{30}^{th}$ dilution. Red: 1641, Green: 1754.25, and Blue: 1219.25.

Figure 10A:
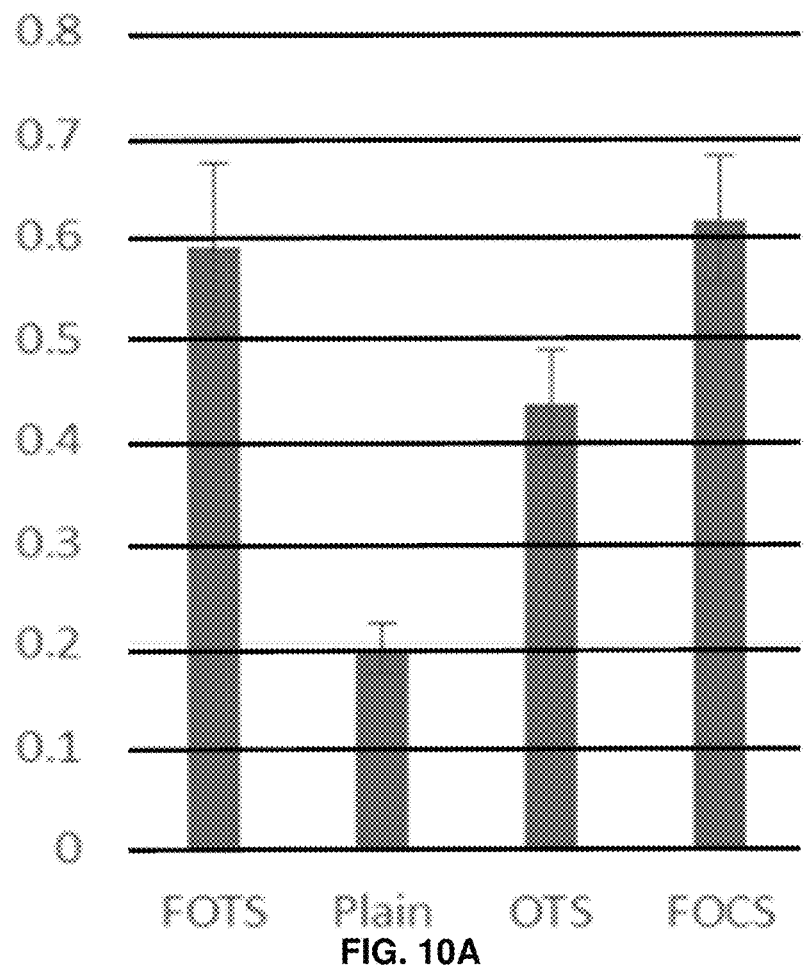
FIG. 10A shows coatings modify the photo-electric properties of the surface. The photo-induced charge transfer in response to a pulsed 533 nm laser is measured. All modified surfaces saw an increased photo-induced charge transfer in comparison to silicon.
Figure 10B:
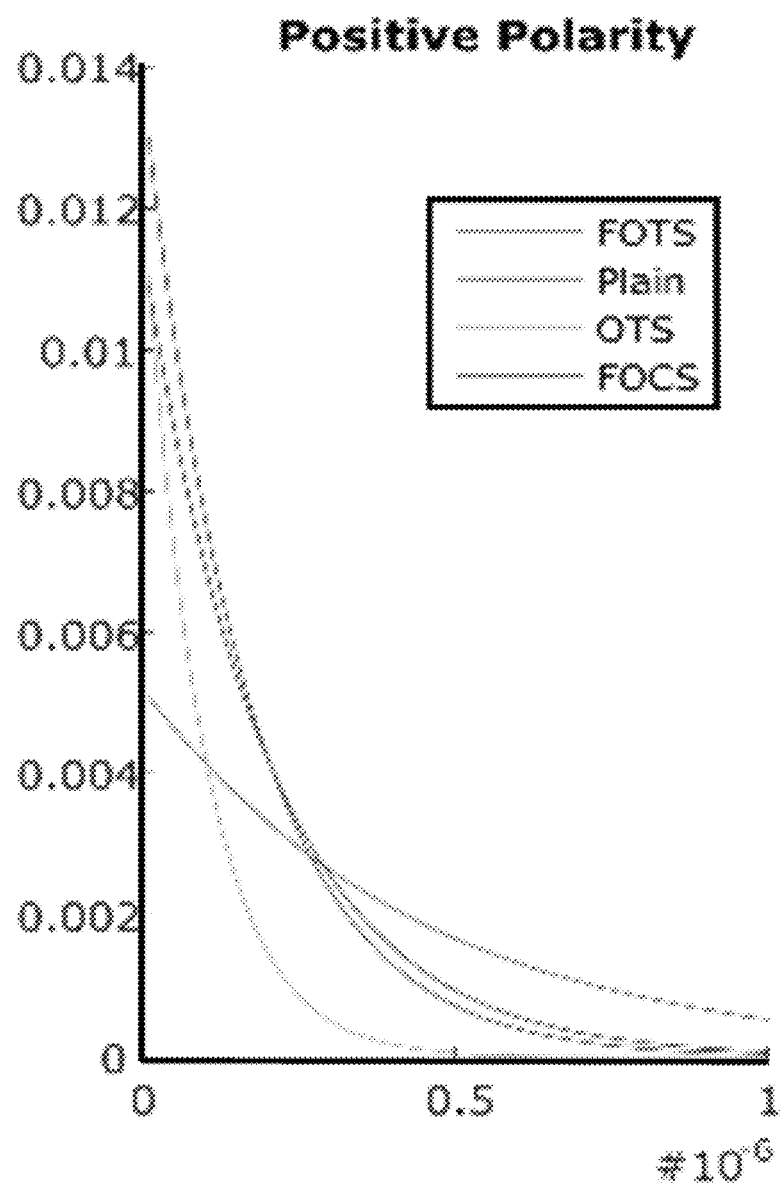
FIG. 10B shows coatings modify the photo-electric properties of the surface. The photo-induced charge transfer in response to a pulsed 533 nm laser is measured. All modified surfaces saw a shifting charge dissipation towards larger amplitudes and faster decay times—plotted here as the average exponential decay for each condition.

FIGS. 10A and 10B show coatings modify the photoelectric properties of the surface.

Figure 11:
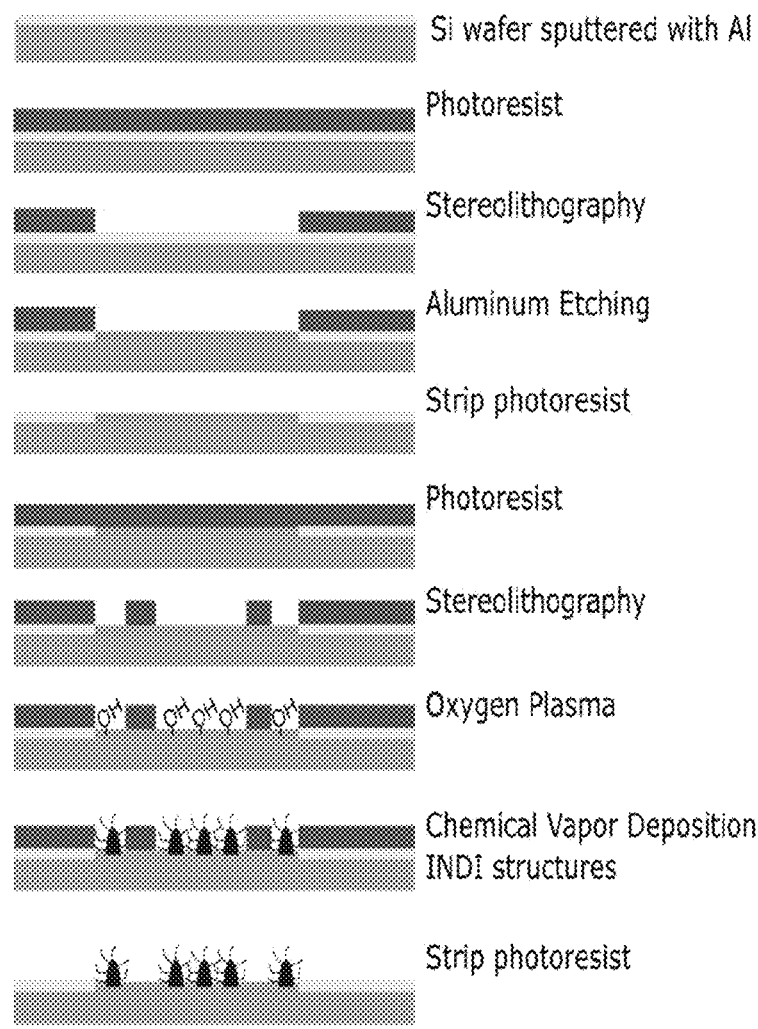
FIG. 11 shows the steps for the manufacture of micro-patterned INDI (µINDI) arrays suited for mass production and high-throughput screening applications. µINDI take advantage of photolithographic liftoff to generate micro-patterns for INDI-MS. Aluminum traces are used as a visual cue for the array. The covalent attachment of the FOTS molecules ensures they are not washed away during acetone liftoff. An 1456 INDI-MS array can be manufactured on a 1.5 inch×3.5 inch wafer silicon wafer.

FIG. 11 shows the steps for the manufacture of micro-patterned INDI (µINDI) arrays suited for mass production and high-throughput screening applications. µINDI take advantage of photolithographic liftoff to generate micro-patterns for INDI-MS. Aluminum traces are used as a visual cue for the array. The covalent attachment of the FOTS molecules ensures they are not washed away during acetone liftoff. An 1456 INDI-MS array can be manufactured on a 1.5 inch×3.5 inch wafer silicon wafer.

Figure 12:
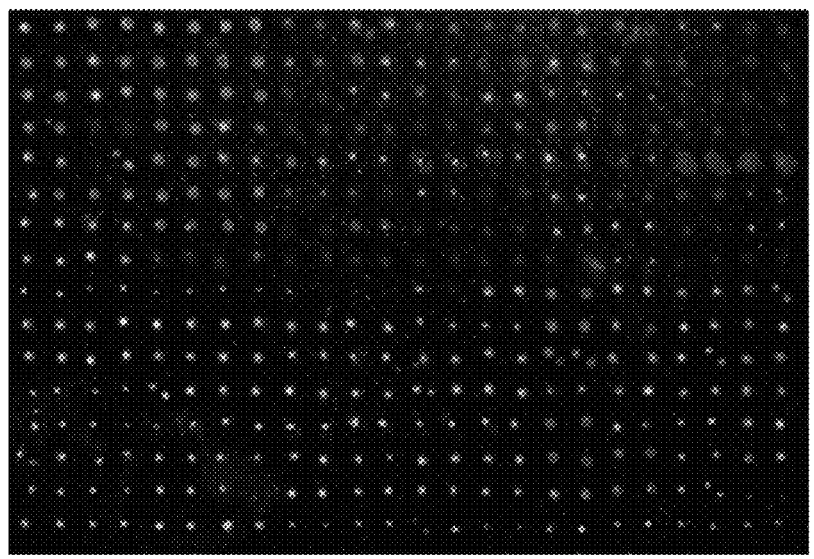
FIG. 12 shows an example of an enzymatic screen/large array.

FIG. 12 shows an example of an enzymatic screen/large array.

Conclusions

The results demonstrate: Vapor-deposited FOTS film are cheap and mass producible. High sensitivity of SALDI substrate for applicable molecules.

References cited in Example 2:
(1) Oyola-Reynoso, S.; Tevis, I. D.; Chen, J.; Chang, B. S.; Çinar, S.; Bloch, J.-F.; Thuo, M. M. *J. Mater. Chem. A* 2016, 4 (38), 14729-14738.
(2) Gao, J.; De Raad, M.; Bowen, B. P.; Zuckermann, R. N.; Northen, T. R. *Anal. Chem.* 2016, 88 (3), 1625-1630.
(3) Law, K. P.; Larkin, J. R. *Anal. Bioanal. Chem.* 2011, 399 (8), 2597-2622.
(4) Northen, T. R.; Yanes, O.; Northen, M. T.; Marrinucci, D.; Uritboonthai, W.; Apon, J.; Golledge, S. L.; Nordström, A.; Siuzdak, G. *Nature* 2007, 449 (7165), 1033-1036.

(5) Northen, T. R.; Yanes, O.; Northen, M. T.; Marrinucci, D.; Uritboonthai, W.; Apon, J.; Golledge, S. L.; Nordström, A.; Siuzdak, G. *Nature* 2007, 449 (7165), 1033-1036.
(6) Kurczy, M.; Northen, T.; Trauger, S.; Siuzdak, G. In *In Mass Spectrometry Imaging of Small Molecules*; He, L., E., Ed.; Springer: New York, 2015; p 141.
(7) Northen, T. R.; Yanes, O.; Northen, M. T.; Marrinucci, D.; Uritboonthai, W.; Apon, J.; Golledge, S. L.; Nordström, A.; Siuzdak, G. *Nature* 2007, 449 (7165), 1033-1036.
(8) Dimitrakopoulos, B. C. D.; Malenfant, P. R. L. 2002, No. 2,99-117.
(9) Oyola-Reynoso, S.; Tevis, I. D.; Chen, J.; Chang, B. S.; Çinar, S.; Bloch, J.-F.; Thuo, M. M. *J. Mater. Chem. A* 2016, 4 (38).

The preceding publications are hereby incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for ionizing a target, comprising: providing a semiconductor substrate comprising a self-assembled, nanostructured fluorocarbon film; applying a plurality of nanoparticles to the substrate such that the plurality of nanoparticles are bound to the nanostructured fluorocarbon film on the substrate; delivering a sample solution comprising a target to the substrate such that the target binds to the plurality of nanoparticles to form a target-loaded substrate; irradiating the target-loaded substrate; and, passive sample drying of the target-loaded substrate whereby undesired contaminants in the sample solution are extracted from the target-loaded substrate; wherein the semiconductor substrate comprises a semiconductor selected from the group consisting of a Group IV semiconductor, a Group I-VII semiconductor, a Group II-VI semiconductor, a Group III-V semiconductor, a sphaelerite structure semiconductor, a Wurtzite Structure Compound, a I-II-VI2 semiconductor, and silicon; wherein each nanoparticle has a diameter of 2 to 4 nm, and the plurality of nanoparticles has a nanoparticle to nanoparticle spacing of about 75 to 200 nm.

2. The method of claim 1, wherein irradiating the target-loaded substrate comprises irradiating the target-loaded substrate with a laser, an ion beam, or any combination thereof.

3. The method of claim 2, wherein delivering a target to the substrate comprises contacting a sample comprising the target to the substrate.

4. The method of claim 3, wherein the sample is a biological sample, an environmental sample, a clinical sample, a forensic sample, or a combination thereof.

5. The method of claim 1, wherein the target is selected from the group consisting of lipids, amino acids, small molecules, peptides, drugs, proteins, and any combination thereof.

6. The method of claim 5, wherein the sample comprises a tissue, a cell, a biofluid, or a combination thereof.

7. The method of claim 1, wherein the nanoparticle comprises Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon.

8. The method of claim 7, wherein the nanoparticle is a composite nanoparticle comprising a coating comprising Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon.

9. The method of claim 8, wherein the composite nanoparticle comprises Gold, Silver, Iron Oxide, Titanium Dioxide, Silicon Dioxide, Silicon, Platinum, Selenium, Cadmium, Cadmium, Tellurium, Cadmium Selenium, Mercury Tellurium, Aluminum, Aluminum Oxide, Zinc, Zinc Oxide, Titanium Silicon Oxide, or Carbon coated by the coating.

10. The method of claim 7, wherein the nanoparticle is Gold.

11. The method of claim 7, wherein the nanoparticle is a halogenated nanoparticle.

12. The method of claim 11, wherein the nanoparticle is a fluorinated Gold nanoparticle (AuNP).

13. The method of claim 1, wherein the semiconductor comprises a semiconductor selected from the group consisting of diamond, CuF, CuCl, CuBr, CuI, AgBr, AgI, BeO, BeS, BeSe, BeTe, BePo, MgTe, ZnO, ZnS, ZnSe, ZnTe, ZnPo, CdS, CdSe, CdTe, CdPo, HgS, HgSe, HgTe, BN, BP, BAs, AlN, AlP, AlAs, AlSb, GaN, GaP, GaSb, InN, InAs, InSb, MnS, MnSe, 3-SiC, Ga2Te3, In2Te3, MgGeP2, ZnSnP2, ZnSnAs2, NaS, MnSe, SiC, MnTe, Al2S3, Al2Se3, CuAlS2, CuAlSe2, CuAlTe2, CuGaS2, CuGaSe2, CuGaTe2, CuInS2, CuInSe2, CuInTe2, CuTIS2, CuTISe2, CuFeS2, CuFeSe2, CuLaS2, AgAS2, AgAlSe2, AgAlTe2, AgGaS2, AgGaSe2, AgGaTe2, AgInS2, AgInSe2, AgInTe2, AgFeS2, and silicon.

14. The method of claim 1, wherein the semiconductor comprises a p-type semiconductor.

15. The method of claim 1, wherein the semiconductor comprises crystalline silicon.

16. The method of claim 1, wherein the semiconductor has a <100> orientation.

17. The method of claim 1, wherein the substrate is a black silicon substrate.

18. The method of claim 1, wherein the target is a constituent of a sample selected from a biological sample, an environmental sample, a clinical sample, a forensic sample, or a combination thereof.

* * * * *